United States Patent [19]

Sera et al.

[11] 4,137,082
[45] Jan. 30, 1979

[54] PHOTOGRAPHIC LIGHT-SENSITIVE MATERIAL HARDENED WITH A VINYLSULFONYL COMPOUND

[75] Inventors: Hidefumi Sera; Tsumoru Ishii; June Yamaguchi; Hisashi Shiraishi, all of Minami-ashigara, Japan

[73] Assignee: Fuji Photo Film Co., Ltd., Minami-ashigara, Japan

[21] Appl. No.: 837,248

[22] Filed: Sep. 27, 1977

[30] Foreign Application Priority Data

Sep. 27, 1976 [JP] Japan .................. 51-115611

[51] Int. Cl.$^2$ ............................................. G03C 1/30
[52] U.S. Cl. ............................... 96/111; 260/117; 106/125; 260/551 S
[58] Field of Search ............... 96/111; 260/117, 551 S; 106/125

[56] References Cited

U.S. PATENT DOCUMENTS 3,868,257  2/1975  Horii et al. ..................... 96/111

FOREIGN PATENT DOCUMENTS 49-24435  4/1974  Japan ........................ 96/111

*Primary Examiner*—Won H. Louie, Jr.
*Attorney, Agent, or Firm*—Sughrue, Rothwell, Mion, Zinn and Macpeak

[57] ABSTRACT

A photographic silver halide light-sensitive material having at least one hydrophilic colloid layer containing (a) gelatin and/or a gelatin derivative and (b) at least one compound represented by the following general formula (I) or (II):

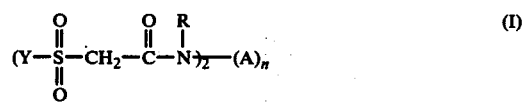

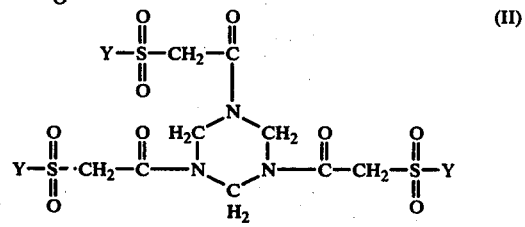

wherein Y represents a vinyl group; A represents a divalent group; R, which may be the same or different, each represents a hydrogen atom or a hydrocarbon group having 1 to 4 carbon atoms; and $n$ is 0 or 1. The compounds of the general formulas (I) and (II) are novel class of gelatin hardeners which are particularly suitable for use in silver halide photographic light-sensitive materials.

6 Claims, No Drawings

PHOTOGRAPHIC LIGHT-SENSITIVE MATERIAL HARDENED WITH A VINYLSULFONYL COMPOUND

BACKGROUND OF THE INVENTION

1. Field of the Invention

The present invention relates to a photographic light-sensitive material, and more particularly, it relates to a silver halide photographic light-sensitive material in which gelatin is used as a binder.

2. Description of the Prior Art

Photographic light-sensitive materials are composed of a silver halide light-sensitive emulsion layer, an emulsion protective layer, a filter layer, an intermediate layer, an antihalation layer, a backing layer, a film support subbing layer, a baryta layer, a film support and the like. Usually, gelatin is used as the main constituent of these layers other than the film support.

These photographic materials containing gelatin are treated with various aqueous solutions having different pH's and temperatures. A conventional gelatin layer has poor water resistance and swells excessively in an aqueous solution, so that the mechanical strength is greatly reduced, and, in an extreme case, the gelatin layer sometimes dissolves out, particularly when the gelatin layer is in an aqueous solution having a high temperature of above 30° C or a highly alkaline aqueous solution.

These properties are fatal defects as physical properties of the layers of the photographic light-sensitive material.

In order to improve these properties of gelatin, many compounds are known and can be effectively used. Many compounds are known which are used as hardeners in the production of photographic light-sensitive materials. Examples are formaldehyde, glutaraldehyde and like aldehyde type compounds; compounds having a reactive halogen as described in U.S. Pat. No. 3,288,775 and so on; compounds containing a reactive ethylenically unsaturated bond as described in U.S. Pat. No. 3,635,718 and so on; aziridine type compounds as described in U.S. Pat. No. 3,017,280; epoxy compounds as described in U.S. Pat. No. 3,091,537; and halocarboxyaldehydes such as mucochloric acid, dioxanes such as dihydroxydioxane and dichlorodioxane, or inorganic hardeners such as chromium alum and zirconium sulfate.

However, most of these known gelatin hardeners have serious defects when they are used in photographic light-sensitive materials, in that the hardening effect is insufficient, in that the gelatin hardening rate is not sufficiently fast, so that film hardening slowly proceeds with the passage of time after the production of the photographic materials (i.e., after-hardening), in that harmful effects on photographic light-sensitive materials occur (particularly, an increase of fog, a decrease of sensitivity, etc.) in that the hardening effect is destroyed by other photographic additives which are present, in that they adversely affect other photographic additives (for example, color forming couplers for color photographic light-sensitive materials), in that the preparation thereof is difficult and a large scale of production is not appropriate, in that the hardeners per se are unstble and storage thereof are difficult, and the like. Further, some of them have a quite bad odor which causes a decrease in work efficiency during production thereof or which is harmful to the human body.

It is also known that hardeners having an active vinyl group are relatively advantageous. For example, divinylsulfone, which is an example thereof, is not practically used due to its quite harmful effect on the human body. The compounds having a vinylsulfonyl group as described in German Patent Publication No. 1,100,942, U.S. Pat. No. 3,490,911, etc., are compounds in which such a defect is improved.

These vinylsulfone type hardeners have advantages as a hardener in that they have generally a high hardening rate and a small after-hardening effect which is the variation of hardening effect with the passage of time, in that they have less harmful effects on photographic properties such as fog formation, desensitization, etc., and in that they have relatively less adverse affects on color photographic emulsions such as decoloration, etc.

However, these vinylsulfone compounds are expensive or they require a special method in which a large amount of organic solvents are used in order to use these compounds. The vinylsulfonyl compounds having an acylamide bond as described in U.S. Pat. No. 3,868,257 and Japanese Patent Application (OPI) No. 24435/74 are examples.

It should be noted, however, that the hardener in question is merely one component of many kinds of additives used in a photographic light-sensitive material which is a relatively complex system. That is, finished photographic light-sensitive materials occasionally come into contact with an atmosphere of formaldehyde vapor or they are influenced by vapors of volatile aldehydes such as methyl glyoxal, acetoaldehyde, etc., which is generated from a film support or a film support subbing layer when the photographic materials are stored under a condition of a relatively high temperature and high humidity before they are used.

In such circumstances fog formation generally occurs and, in the case of color photographic light-sensitive materials, undersirable photographic effects such as inhibition of color development, discoloration, etc., due to the reaction of a color coupler and such a vapor are observed.

It is also known that a urea type compound or a compound having an active methylene group such as dimedone as described in U.S. Pat. Nos. 2,895,827; 3,652,278, etc., is effective as a technique for preventing adverse photographic effects due to aldehyde type vapors.

However, some kinds of ureas can react with a vinylsulfonyl type hardener and so either or both of the effects of a hardener or an aldehyde scavenger by the urea are lost. In order to prevent such a defect, the use of an acyclic urea and a vinylsulfonyl hardener is described in U.S. Pat. No. 3,811,891. However, a urea type compound is generally known as hydrogen bond forming agent. That is, it has the effect for destroying the setting property, i.e., the reversible property between a sol and a gel of gelatin which is one of the big advantages why gelatin is used as photographic binder and thus the use of ureas in the production of photographic ligh-sensitive material is not preferred.

SUMMARY OF THE INVENTION

It has now been found that a photographic light-sensitive material substantially free from the above-described defects can be obtained by using, in at least one hydrophilic colloid layer therof which contains gelatin and/or a gelatin derivative, a compound represented by the following general formula (I) or (II):

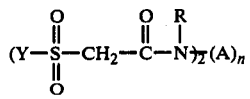
(I)

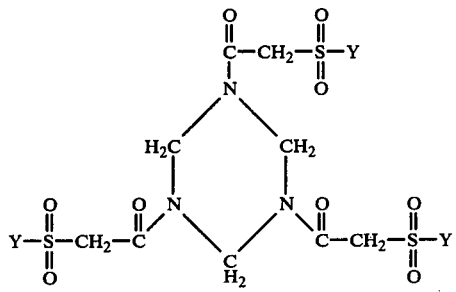
(II)

wherein Y represents a vinyl group; A represents a divalent group; R represents a hydrogen atom or a hydrocarbon group having 1 to 4 carbon atoms, preferably an alkyl group such as a methyl group, an ethyl group, etc. The two R's which are present in the same molecule can be the same or different; and n is 0 or 1. Any divalent group can be used as A but preferably a cyclic hydrocarbon group having 1 to 10 carbon atoms such as an m-phenylene group, an acyclic hydrocarbon group such as a methylene group, an ethylene group, a trimethylene group, a tetramethylene group can be used. One to three of the carbon atoms thereof can be replaced by a hetero atom such as a nitrogen atom, a sulfur atoms, an oxygen atom, etc. Suitable examples of groups containing hetero atom(s) include a group containing a —(CH$_2$CH$_2$O)$_2$—CH$_2$CH$_2$— group, a —CH$_2$CH$_2$OCH$_2$CH$_2$— group, etc. More preferably A is a divalent branched or straight chain hydrocarbon group having 1 to 5 carbon atoms. Also, the chain can be substituted, for example, with one or more of an alkoxy group having 1 to 4 carbon atoms such as a methoxy group, an ethoxy group, etc., a halogen atom such as a chlorine atom, a bromine atom, etc., a hydroxy group, an acetoxy group and the like.

DETAILED DESCRIPTION OF THE INVENTION

The compounds used in the present invention are all novel compounds and can be prepared in good yield using known reactions.

For instance, the compound represented by the general formula (I) or (II) can be prepared from the compound represented by the following general formulas (II) and (IV), respectively, or from other similar compounds.

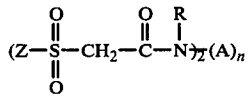
(III)

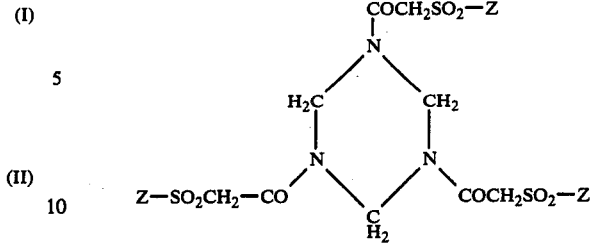
(IV)

wherein R, A and n each has the same meaning as defined in the general formula (I); and Z represents X—CH$_2$CH$_2$—. A chloroethylsulfonyl group, i.e., where X is a chlorine atom in the above formula, is obtained as follows. A chloroacetic acid derivative which is prepared by reacting ClCH$_2$COCl with a substantially stoichiometric amount of a diamine of the formula H$_2$N—A—NH$_2$ wherein A is as described above in a solvent such as water or an organic solvent at a temperature of about −70° to about 100° C in the presence of a catalyst such as NaOH, KOH, Na$_2$CO$_3$, triethylamine, triethylenediamine, etc., is reacted with a substantially stoichiometric amount of β-mercaptoethanol in a solvent such as water, ethanol, etc., at a temperature of about 0° C to about 100° C in the presence of a catalyst such as NaOH, KOH, Na$_2$CO$_3$, triethylamine, triethylenediamine, etc., to form a (β-hydroxyethylthio)acetic acid derivative. Then the hydroxy group of the (β-hydroxyethylthio)acetic acid derivative is chlorinated with a substantially stoichiometric amount or more of thionyl chloride in an organic solvent such as chloroform, benzene, acetonitrile, etc., at a temperature of about 0° to about 80° C using a catalyst such as morpholine, dimethylformamide, etc., e.g., as described in Japaneses Patent Application (OPI) No. 24435/74, and subsequently the thioether bond thereof is oxidized with a substantially stoichiometric amount or more of hydrogen peroxide in a solvent such as acetic acid, water, etc., at a temperature of about 50° to 100° C in the presence of a catalyst such as acetic acid, phosphoric acid, tungstic acid, etc., to form a chloroethylsulfonylacetic acid derivative (e.g., as described in Japanese Patent Application (OPI) No. 24435/74). Alternatively, the thioether bond can be initially oxidized to form a hydroxyethylsulfonylacetic acid derivative and then the hydroxy group thereof is chlorinated.

A vinyl group can be obtained by the dehydrochlorination of a chloroethyl group and can be conducted using a stoichiometric amount of the thus-obtained chloroethylsulfonylacetic acid derivative and triethylamine, triethylenediamine or 1,8-diazobicyclo[5,4,0]-7-undecene in a solvent such as dimethylformamide, acetone, etc., at a temperature of about −20° to 60° C (e.g., as described in Japanese Patent Application (OPI) No. 24435/74). In the case where X represents an acyloxy group such as an acetyloxy group, a tosyloxy group, etc., a quaternary ammonium salt, a sulfuric acid monoester and the like, in addition to a halogen atom, a vinyl group can be obtained by dehydrochlorination.

Typical examples of the compounds which can be used in the present invention and synthesis examples thereof are given below, but the present invention is not to be construed as being limited to these examples.

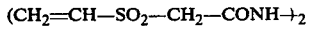
(1)

$(CH_2=CH-SO_2-CH_2-CONH)_2CH_2$ (2)

$(CH_2=CH-SO_2-CH_2-CONH-CH_2)_2$ (3)

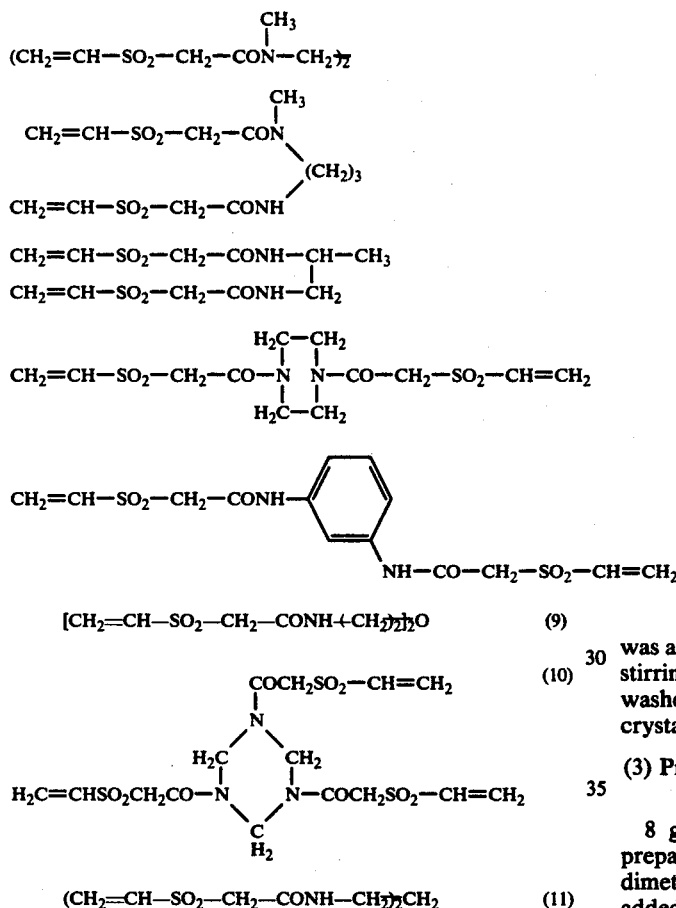

$[CH_2=CH-SO_2-CH_2-CONH-CH_2]_2O$ (9)

$(CH_2=CH-SO_2-CH_2-CONH-CH_2)_2CH_2$ (11)

In the Examples and Synthesis Examples given herein, all parts, percents, ratios and the like are by weight unless otherwise indicated.

SYNTHESIS EXAMPLE 1

Synthesis of Compound 3

(1) Preparation of ethylenebischloroacetamide 23 g of chloroacetic chloride was added dropwise to a solution containing 6 g of ethylenediamine, 12 g of sodium hydroxide and 70 ml of water with stirring at 0° to 5° C. After the completion of the addition, the temperature increased gradually to room temperature (about 20°–30° C) and the reaction mixture was filtered. The crystals obtained were washed with water and dried to obtain 15.1 g of crystals.

(2) Preparation of ethylenebis(β-chloroethylsulfonyl)acetamide 10 g of sodium salt of 2-mercaptoethanol was added to 70 ml of methanol and to which 14.8 g of ethylenebischloroacetamide prepared as described above was added with stirring at below 20° C. After stirring for 5 hours, methanol was distilled off, 70 ml of chloroform was added to the residue and 15 g of thionyl chloride was added dropwise thereto at room temperature. The mixture was gradually heated to reflux, refluxed for about 2 hours, and filtered. The crystals obtained were washed with acetone and then water and dried. The crystals were added to 100 ml of glacial acetic acid and 20 ml of a 35% aqueous solution of hydrogen peroxide was added dropwise with stirring at below 60° C. After stirring for 3 hours at 60° C the precipitate was filtered, washed with water and dried to obtain 9.8 g of white crystals having a melting point of 214° C.

(3) Preparation of ethylenebis(vinylsulfonyl)acetamide (Compound 3)

8 g of ethylenebis(β-chloroethylsulfonyl)acetamide prepared as described above was dissolved in 50 ml of dimethylformamide and 3 ml of triethylamine was added to the solution with stirring at room temperature. After standing overnight the filtrate was concentrated under reduced pressure to obtain white crystals. After recrystallization from methanol, 4.7 g of white crystals having a melting point of 147° to 150° C was obtained.

SYNTHESIS EXAMPLE 2

(1) Preparation of N,N'-bischloroacetylpiperazine

By reacting 8.6 g of piperazine with 23 g of chloroacetic chloride in the same manner as described in Synthesis Example 1, 36 g of crystals of the title compound were obtained.

(2) Preparation of N,N'-bis(β-chloroacetylsulfonylacetyl)piperazine 24 g of N,N'-bischloroacetylpiperazine prepared as described above and 20 g of the sodium salt of 2-mercaptoethanol were reacted in the same manner as described in Synthesis Example 1. The reaction mixture was oxidized with 25 g of aqueous hydrogen peroxide (35%) and then was chlorinated with 25 g of thionyl chloride to obtain 24.5 g of white crystals having a melting point of 167° to 171° C.

(3) Preparation of N,N'-bis(vinylsulfonylacetyl)piperazine 21 g of N,N'-bis(β-chloroethylsulfonylacetyl)piperazine prepared as described above was dehydrochlorinated in the same mannner as described in Synthesis Example 1 to obtain 12.7 g of white crystals having a melting point of 215° C (gradual decomposition).

According to the present invention the compound represented by the general formula (I) or (II) can be incorporated into any hydrophilic colloid layer including a surface protective layer, an interlayer, a filter layer, an antihalation layer, a subcoating layer, a backing layer, etc., but it is particularly preferred for the compound of the general formula (I) or (II) to be incorporated into a silver halide photographic light-sensitive emulsion layer. The period when the compound is added to the hydrophilic colloid layer is not critical, but it is preferred for the compound to be added to a coating solution for the hydrophilic colloid layer and then the coating solution coated.

The amount of the compound of the present invention used can be varied as desired depending on the desired objective. The amount used generally ranges from about 0.1 to about 10 wt%, preferably from 0.5 to 5 wt%, based on the weight of dry gelatin. When the compound of the present invention used in an amount more than about 10 wt% based on the dry gelatin, sometimes the gelatin layer is excessively hardened and this is not preferred from the standpoint of the photographic properties. On the other hand, with the use of an amount less than about 0.1 wt%, a sufficient hardening cannot be obtained even after drying, and the film strength is insufficient. If the amount used is in the above range, the hardening of the gelatin proceeds smoothly, which is a feature of the compound of the present invention, and hardening can be exerted satisfactorily.

When the compound is used as a hardener in a gelatin-containing photographic light-sensitive material according to the present invention, the compound does not cause a degradation of photographic properties such as fog formation, desensitization, etc. Further, adverse affects such as an interaction with a color coupler in a color photographic light-sensitive material is substantially not observed. Moreover, the compound maintains a high hardening rate and no after-hardening, which is commonly a property of vinylsulfonyl type hardeners, occurs.

Also, the compound used in the present invention has an acylamide bond in the molecule just as the hardeners described in U.S. Pat. No. 3,868,257 and Japanese Patent Application (OPI) No. 24435/74, and this it possesses a high affinity for water or gelatin and other features as described in the above patent applications.

More importantly, the compound used in the present invention substantially prevents fog formation in a formaldehyde atmosphere (formaldehyde fog). Moreover, the hardening effect per unit weight of the compound according to the present invention is higher than that of a vinylsulfonyl type hardener having a relatively similar chemical structure, i.e.,

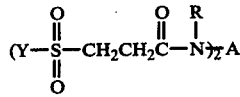

wherein A, R and Y are the same as described above. This is an important factor which leads to a reduction in the amount added and a decrease in the production cost.

It is presumed that these two properties which are apparently independent of each other depend on the active methylene group by which the compound according to the present invention is characterized. That is, in the compound used in the present invention, a carbonyl moiety and a sulfonyl moiety are bonded through only one carbon atom and thus the methylene moiety is rendered so active that it is capable of fixing an aldehyde type vapor, resulting in the prevention of formaldehyde fog. Also, it is believed that the electron-attracting effect of the carbonyl moiety is not sheltered by only one carbon atom but influences the sulfonyl moiety and, therefore, the reactive moiety is activated to cause an increase in the hardening effect.

The compounds of the present invention can be used individually or as mixtures of two or more thereof. Further, the compounds of the present invention can be used in combination with other known hardeners. Suitable known hardeners include, for example, formaldehyde, glutaraldehyde and like aldehyde type compounds; diacetyl, cyclopentadione and like ketone compounds; bis(2-chloroethylurea), 2-hydroxy-4,6-dichloro-1,3,5-triazine and other compounds containing a reactive halogen, as described in U.S. Pat. Nos. 3,288,775 and 2,732,303 and British Pat. Nos. 974,723 and 1,167,207; divinylsulfone, 5-acetyl-1,3-diacryloyl-hexahydro-1,3,5-triazine and other compounds containing reactive olefin, as described in U.S. Pat. Nos. 3,635,718 and 3,232,763 and British Pat. No. 994,869; N-hydroxymethylphthalimide and other N-methylol compounds as described in U.S. Pat. Nos. 2,732,316 and 2,586,168; isocyanates as described in U.S. Pat. No. 3,103,437; aziridine compounds as described in U.S. Pat. Nos. 3,017,280 and 2,983,611; acid derivatives as described in U.S. Pat. Nos. 2,725,294 and 2,725,295; carbodiimide type compounds as described in U.S. Pat. No. 3,100,704; epoxy compounds as described in U.S. Pat. No. 3,091,537; isoxazole type compounds as described in U.S. Pat. Nos. 3,321,313 and 3,543,292; halocarboxyaldehydes such as muchchloric acid, dioxane derivatives such as dihydroxydioxane and dichlorodioxane; and inorganic hardeners such as chromium alum and zirconium sulfate. Instead of above compounds, the compounds of the present invention can be used in combination with precursors of the above-described known hardening compounds, such as alkali metal bisulfite aldehyde adducts, methylol derivatives of hydantoin and primary fatty nitroalcohols, etc. When the compound of the present invention is used in combination with other hardeners, the amount of the compound(s) of the present invention used can be selected as desired depending on the object and the effect.

For the photographic materials to which the present invention is effective, a silver halide emulsion can be prepared by mixing a water-soluble silver salt (e.g., silver nitrate) solution and a water-soluble halide (e.g., potassium bromide) solution in the presence of a water-soluble polymer (e.g., gelatin) solution. Useful silver halides include silver chloride, silver bromide and mixed silver halides such as silver chlorobromide, silver iodobromide and silver chloroiodobromide. These photographic emulsions are described in C. E. K. Mees & T. H. James, *The Theory of the Photographic Process*, 3rd Ed., MacMillan, New York (1966), P. Glafkides, *Chimie Photographique*, Paul Montel, Paris (1957) and the like, and can be prepared using the known ammonia method, neutral method, acid method and the like.

The above silver halide emulsions can be chemically sensitized in a conventional manner, if desired. Suitable chemical sensitizers include, for example, chloroaurate, auric-chloride and like gold compounds as described in U.S. Pat. Nos. 2,399,083; 2,540,085; 2,597,856 and 2,597,915; salts of noble metals such as platinum, palladium, iridium, rhodium and ruthenium as described in U.S. Pat. Nos. 2,448,060; 2,540,086; 2,566,245; 2,566,263 and 2,598,079; sulfur compounds forming silver sulfide upon reaction with a silver salt, as described in U.S. Pat. Nos. 1,574,944; 2,410,689; 3,189,458 and 3,501,313; stannous salts, amines and other reducing materials, as described in U.S. Pat. Nos. 2,487,850; 2,518,689; 2,521,925; 2,521,926; 2,694,637; 2,983,610 and 3,201,254.

The photographic emulsion containing the hardener of the present invention can, if desired, be spectrally sensitized or supersensitized using cyanine, merocyanine, carbocyanine and like cyanine dyes individually or in combination, or in combination with styryl dyes.

Such dye sensitizing techniques are well known and are described in U.S. Pat. Nos. 2,493,748; 2,519,001; 2,977,229; 3,480,434; 3,672,897; 3,703,377; 2,688,545; 2,912,329; 3,397,060; 3,615,635; 3,268,964, British Pat. Nos. 1,195,302; 1,242,588 and 1,293,862, German Patent Applications (OLS) Nos. 2,030,326 and 2,121,780, Japanese Patent Publications Nos. 4936/68; 14030/69 and 10773/68, U.S. Pat. Nos. 3,511,664; 3,522,052; 3,527,641; 3,615,613; 3,615,632; 3,617,295; 3,635,721; 3,694,217, British Pat. Nos. 1,137,580 and 1,216,203 and the like. The sensitizing material(s) used can freely be selected depending on the wavelength range to which the photographic material is to be sensitized, the sensitivity desired, the end use objective and the like.

Various compounds can be added to the above photographic emulsion in order to prevent a reduction of sensitivity and the generation of fog during manufacturing, storage or processing of the photographic material. Many compounds are known as such compounds, for example, 4-hydroxy-6-methyl-1,3,3a,7,-tetrazaindene, 3-methylbenzothiazole, 1-phenyl-5-mercaptotetrazole, and like heterocyclic compounds, mercury-containing compounds, mercapto compounds and metal salts. Examples of suitable compounds are described in the following patents as well as in C. E. K. Mees & T. H. James, *The Theory of the Photographic Process*, 3rd Edition, pp. 344–349, MacMillan, New York (1966), and the original literature references cited therein, U.S. Pat. Nos. 1,758,576; 2,110,178; 2,131,038; 2,173,628; 2,697,040; 2,304,962; 2,324,123; 2,394,198; 2,444,605 - 8; 2,566,245; 2,694,716; 2,697,099; 2,708,162; 2,728,663 - 5; 2,576,536; 2,824,001; 2,843,491; 2,886,437; 3,052,544, 3,137,577; 3,220,839; 3,226,231; 3,236,652; 3,251,691; 3,252,799; 3,287,135; 3,326,681; 3,420,668; 3,622,339, British Pat. Nos. 893,428; 403,789; 1,173,609 and 1,200,188.

Any of alkali treated gelatin obtained by immersion in an alkali bath (lime-treatment) before gelatin extraction, acid treated gelatin obtained by immersion in an acid bath and enzyme treated gelatin as described in *Bull. Soc. Sci. Photo. Japan,* No. 16, page 30, 1966 may be used as the gelatin, which is mainly used for a binder of a hydrophilic colloid layer according to the present invention. Further, the present invention is applicable to the low molecular weight gelatin which is obtained by partial hydrolysis of gelatin through heating in water bath or interaction with a protenase. A suitable amount of gelatin and/or gelatin derivative which is used in this invention as the binder of the hydrophilic colloid layer is about 1 mg/m$^2$ to about 50 g/m$^2$, preferably 0.01 to 20 g/m$^2$.

The gelatin to which the compound of the present invention is applied may, if desired, be replaced in part by colloidal albumin, casein, cellulose derivatives such as carboxymethylcellulose and hydroxyethylcellulose, agar, sodium alginate, starch derivatives and like saccharide derivatives, and synthetic hydrophilic colloids such as polyvinyl alcohol, poly-N-vinyl pyrrolidone, polyacrylic acid copolymers, polyacrylamide and the derivatives thereof. In addition, the gelatin may be replaced by a gelatin derivative which is obtained by reacting the amino, imino, hydroxy or carboxyl groups present as functional groups in the gelatin molecule with an agent containing a group capable of reacting with such functional groups, or may be replaced by a graft gelatin in which a molecular chain of another polymeric material is grafted to gelatin.

The photographic emulsion layer or other layers may contain synthetic polymer compounds, e.g., latex like water-dispersable polymers of vinyl compounds, particularly compounds improving the dimensional stability of the photographic materials, individually or as a mixture (a mixture of different kinds of polymers), or in combination with hydrophilic water-permeable colloids. Many such polymers are described, for example, in U.S. Pat. Nos. 2,853,457; 3,411,911; 3,488,708 and 3,525,620.

A matting agent can be used in the light-sensitive material of the present invention. Particles of water-insoluble organic or inorganic compounds, with an average particle size of about 0.2 $\mu$ to about 10 $\mu$, preferably 0.3 $\mu$ to 5 $\mu$ may be used as matting agents. Examples of suitable organic compounds are water-dispersable vinyl polymers such as polymethyl acrylate, polymethyl methacrylate, polyacrylonitrile, acrylonitrile-$\alpha$-methylstyrene copolymers, polystyrene, cellulose derivatives such as methyl cellulose, ethyl cellulose, cellulose acetate, cellulose acetate propionate, starch derivatives such as carboxy starch, carboxynitrophenyl starch. Examples of inorganic compounds are silicon dioxide; titanium dioxide; magnesium oxide; aluminum oxide; barium sulfate; calcium carbonate; silver chloride and silver bromide desensitized using known methods, glass and the like.

A coupler can be used in the photographic light-sensitive material of the present invention. In this case, diffusion resistant couplers are incorporated in a silver halide emulsion layer. Examples of suitable couplers are 4-equivalent diketomethylene yellow couplers and 2-equivalent diketomethylene yellow couplers, for example, the compounds as described in U.S. Pat. Nos. 3,415,652, 3,447,928, 3,311,476 and 3,408,194; compounds as described in U.S. Pat. Nos. 2,875,057; 3,265,506; 3,409,439; 3,551,155 and 3,551,156; compounds as described in Japanese Patent Applications (OPI) Nos. 26133/72 and 66836/73; 4-equivalent or 2-equivalent pyrazolone magenta couplers and indazolone magenta couplers, for example, the compounds as described in U.S. Pat. Nos. 2,600,788; 2,983,608; 3,062,653; 3,214,437; 3,253,924; 3,419,391; 3,419,808; 3,476,560 and 3,582,322, Japanese Patent Publication No. 20636/70, Japanese Patent Application (OPI) No. 26133/72, $\alpha$-naphthol type cyan couplers and phenol cyan couplers, for example, the compounds as described in U.S. Pat. Nos. 2,474,293; 2,698,794; 3,034,892; 3,214,437; 3,253,924; 3,311,476; 3,458,315; 3,591,383, Japanese Patent Publication Nos. 11304/67 and 32461/69. In addition, the compounds as described in U.S. Pat. Nos. 3,227,554; 3,297,445; 3,253,924; 3,311,476; 3,379,529; 3,516,831; 3,617,291; 3,705,801, German Patent Application (OLS) No. 2,163,811 can be used.

Surface active agents individually or in admixture may be added to the photographic emulsion of the photographic light-sensitive materials of the present invention. Although such surface active agents are generally used as coating aids, they may also be used for other purposes, for example, for the purpose of dispersion, sensitization, improvement of photographic properties, prevention of the generation of static charges and prevention of adhesion.

These surface active agents are classified as naturally occurring surface active agents such as saponin; nonionic surface active agents such as those of the alkylene oxide type, the glycerin type and the glycidol type; cationic surface active agents such as higher alkylamines, quaternary ammonium salts, pyridine and like heterocyclic compounds, phosphoniums and sulfoniums; anionic surface active agents containing acidic groups such as carboxylic acid, sulfonic acid, phosphoric acid, sulfonic acid ester and phosphoric acid ester group; and amphoteric surface active agents such as amino acids, amino sulfonic acids, and sulfates or phosphates of amino alcohols.

Suitable supports for the photographic light-sensitive material according to the present invention include those generally used for photographic light-sensitive materials such as cellulose nitrate films, cellulose acetate films, cellulose acetate butyrate films, cellulose acetate propionate films, polystyrene films, polyethylene terephthalate films, polycarbonate films, and laminates thereof, thin glass films; paper coated with baryta; paper coated or laminated with an α-olefin polymer, particularly a polymer of an α-olefin containing 2 to 10 carbon atoms, such as polyethylene, polypropylene and ethylene-butene copolymers; and a synthetic resin films whose surface has been roughened to thereby improve adhesion to other polymeric materials and to improve the printability thereof as described in Japanese Patent Publication No. 19068/72.

Each layer of the photographic light-sensitive material of the present invention can be coated using various coating methods including dip coating, air knife coating, curtain coating, spray coating, extrusion coating using a hopper as described in U.S. Pat. No. 2,681,294, etc. If desired, two or more layers can be simultaneously coated by methods as described in U.S. Pat. Nos. 2,761,791; 3,508,947; 2,941,898 and 3,526,528.

The photographic light-sensitive materials of the present invention include not only conventional silver halide photographic light-sensitive materials but also photographic light-sensitive materials for the diffusion transfer process.

Further, the compound according to the present invention can be used not only by addition to a photographic light-sensitive material but also by addition to a processing solution.

The present invention will be further explained by reference to the following Examples, but the present invention is not to be construed as being limited to these Examples.

EXAMPLE 1

The compound used in the present invention was added to a 7 wt% aqueous gelatin solution as shown in Table 1 below, and the solution was coated on a cellulose triacetate film at a dry thickness of 10 μ and dried. While storing this sample at 25° C, 60% RH, a part of the sample was removed on the 1st, 7th, 14th and 21st days after coating and the samples were measured in water at 25° C with the degree of swelling (Q) represented by the following formula:

$$Q = \frac{\text{Layer Thickness Increased by Swelling}}{\text{Dry Layer Thickness}}$$

The same measurement was carried out using a sample which had been cured in an atmosphere of 50° C, 80% RH for 2 days. Compound A shown in Table 1 has the following formula.

Compound A

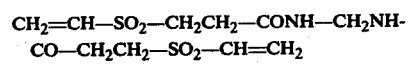

$CH_2=CH-SO_2-CH_2CH_2-CONH-CH_2NH-CO-CH_2CH_2-SO_2-CH=CH_2$

TABLE 1

| Compound | Amount Added (milli mol/g gelatin) | Time after Coating | | | | 50° C 80% RH 2 days |
|---|---|---|---|---|---|---|
| | | 1 day | 7 days | 14 days | 21 days | |
| Control | 0 | 16.1 | 14.8 | 14.0 | 13.8 | 10.5 |
| Compound 1 | 0.05 | 5.3 | 3.0 | 2.8 | 2.9 | 2.8 |
| Compound 3 | 0.05 | 4.9 | 3.3 | 3.1 | 3.2 | 3.0 |
| Compound 9 | 0.05 | 5.7 | 3.4 | 3.2 | 3.2 | 3.1 |
| Compound 10 | 0.05 | 5.3 | 3.5 | 3.3 | 3.1 | 2.9 |
| Compound A | 0.05 | 6.2 | 5.0 | 4.4 | 3.9 | 3.5 |

As can be seen from the results shown in Table 1 above, the compounds of the present invention have a property capable of hardening a gelatin layer to a certain degree of swelling so that it can be used in a photographic material and are high hardening rate type hardeners which do not exhibit a variation in hardening effect with the passage of time, i.e., after-hardening.

EXAMPLE 2

To 1 kg of a high speed silver iodobromide emulsion (iodide content: 5.0 mol%, average particle size: 0.8 μ) which was subjected to optimum reduction sensitization, and gold sensitization, 200 cc of a 0.1% methanol solution of anhydro-9-ethyl-5,5'-diphenyl-3,3'-diethylbenzoxacarbocyanine hydroxide pyridinium salt and 24 cc of a 0.7% solution of anhydro-5,5',6,6'-tetrachloro-1,1'-diethyl-3,3'-di(3-sulfopropyl)-benzimidazolocarbocyanine hydroxide sodium salt as spectral sensitizers, 50 cc of a 1% aqueous solution of 4-hydroxy-6-methyl-1,3,3a,7-tetrazaindene as anti-foggant and 30 cc of a 10% aqueous solution of saponin were added. The emulsion was divided into three portions and to a first portion was added 10 cc of a 2% aqueous solution of 2,4-dichloro-6-hydroxy-s-triazine, as a control, to a second portion was added 5 cc of a 0.3 M methanol solution of Compound 3 of the present invention, and to a third portion was added 5 cc of a 0.3 M methanol solution of Compound A, respectively. Each emulsion was coated on a cellulose triacetate film support having a subbing layer at a dry thickness of 5 μ and dried. Each of these three films was stored at 40° C for 24 hours in a container of a volume of 3 liters in which a solution containing 0, 0.2, 0.4, 0.8 and 1.6 cc of a 37% aqueous formaldehyde solution per 100 cc of a 86 wt% of aqueous glycerol solution, respectively, was placed at the bottom thereof and the air equilibrated and then the degree of swelling (Q) with each film was measured.

which the relative values of the maximum density are also illustrated.

TABLE 3

| Amount of Formaldehyde | Film IV (Control) | | | Film V (Compound 3) | | | Film VI (Compound A) | | |
|---|---|---|---|---|---|---|---|---|---|
| | Fog | Relative Sensitivity | Maximum Density | Fog | Relative Sensitivity | Maximum Density | Fog | Relative Sensitivity | Maximum Density |
| 0 | 0.20 | 100 | 100 | 0.20 | 98 | 98 | 0.20 | 98 | 100 |
| 0.2 | 0.22 | 145 | 85 | 0.21 | 141 | 95 | 0.21 | 141 | 86 |
| 0.4 | 0.26 | 159 | 80 | 0.22 | 145 | 88 | 0.25 | 160 | 81 |
| 0.8 | 0.31 | 174 | 75 | 0.25 | 160 | 84 | 0.30 | 173 | 78 |
| 1.6 | 0.49 | 170 | 68 | 0.32 | 166 | 80 | 0.46 | 178 | 70 |

Further, another sample of each film was exposed using an NSG II type sensitometer and developed for 10 minutes at 20° C with a D-76 developer in order to determine the fog density. Also, the exposure amount required to provide an optical density of fog + 0.2 was measured and the relative sensitivity was determined using the sensitivity of the control sample without contact with formaldehyde being 100. The results obtained are shown in Table 2 below.

TABLE 2

| Amount of Formaldehyde | Film I (control) | | Film II (Compound 3) | | Film III (Compound A) | |
|---|---|---|---|---|---|---|
| | Fog | Relative Sensitivity | Fog | Relative Sensitivity | Fog | Relative Sensitivity |
| 0 | 0.04 | 100 | 0.03 | 95 | 0.04 | 98 |
| 0.2 | 0.06 | 144 | 0.04 | 110 | 0.06 | 143 |
| 0.4 | 0.09 | 138 | 0.06 | 126 | 0.10 | 136 |
| 0.8 | 0.20 | 112 | 0.12 | 130 | 0.19 | 110 |
| 1.6 | 0.32 | 90 | 0.20 | 113 | 0.30 | 85 |
| Degree of Swelling | 2.5 | | 2.8 | | 3.2 | |

As can be seen from the results shown in Table 2, Compound 3 of the present invention has a sufficient function as a hardener and remarkably prevents fog formation due to formaldehyde.

EXAMPLE 3

To an emulsion the same as described above in Example 2, the spectral sensitizers, the anti-foggant and saponin as described in Example 2 were added in the same manner as in Example 2 and further a dispersion which was prepared by dispersing a tri-o-cresyl phosphate solution of 1-(2,4,6-trichlorophenyl)-3-[3-(2,4-di-tert-amylphenoxy-acetamido)benzamide]-5-pyrazolone as magenta coupler into gelatin was added in an amount of 9.5 g of the magenta coupler per mol of silver halide. The emulsion was divided into three portions and Compound 3, Compound A and a Control Compound (2,4-dichloro-6-hydroxy-s-triazine sodium salt) were added to these portions in the same manner as described in Example 2, respectively, and each emulsion was coated on a cellulose acetate support at a coated coupler amount of 1.8 mg/m² and dried. These films were sotred in air equilibrated with a glycerol solution containing formaldehyde in the same manner as in Example 2. Each film was exposed stepwise using an NSG sensitometer through a filter for providing green light exposure (#BPB-53, manufactured by Fuji Photo Film Co., Ltd.) and processed according to the color processing procedure described in Example 1 of German Patent Application (OLS) No. 2,548,897. The density of the magenta dye thus-formed was measured (at 547 nm) and the relative sensitivity was determined using the exposure amount necessary to provide an optical density of fog + 0.2. The results obtained are shown in Table 3 in It is apparent from the results in the above table that the compound of the present invention prevents not only fog formation due to formaldehyde but also does not inhibit color formation of the magenta coupler.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive material comprising a support having thereon at least one silver halide emulsion layer, with at least one hydrophilic colloid layer thereof containing (a) gelatin and/or a gelatin derivative and (b) 0.1 to about 10 wt% based on the weight of dry gelatin or derivative of at least one compound represented by the following general formula (I) or (II):

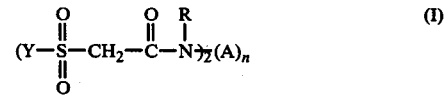

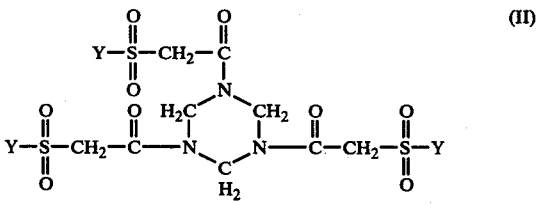

wherein Y represents a vinyl group; A represents a divalent cyclic or acyclic hydrocarbon group having 1 to 10 carbon atoms, one to three of which carbon atoms can be replaced by a hetero atom; R, which may be the same or different, each represents a hydrogen atom or a hydrocarbon group having 1 to 4 carbon atoms; and $n$ is 0 or 1.

2. The photographic light-sensitive material as claimed in claim 1, wherein said divalent group represented by A is a straight or branched chain hydrocarbon group having 1 to 5 carbon atoms.

3. The photographic light-sensitive material as claimed in claim 1, wherein said hydrophilic colloid layer is a gelatin-containing layer.

4. The photographic light-sensitive material as claimed in claim 4, wherein said compound is present in said gelatin-containing layer in an amount of from 0.5 to 5 wt%, based on the weight of the dry gelatin.

5. The photographic light-sensitive material as claimed in claim 1, wherein said R is a hydrogen atom or a methyl group.

6. A method of hardening gelatin in a photographic light-sensitive silver halide material which comprises treating the photographic light-sensitive silver halide material with a compound represented by the following general formula (I) or (II):
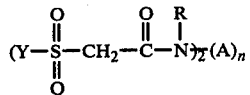 (I)
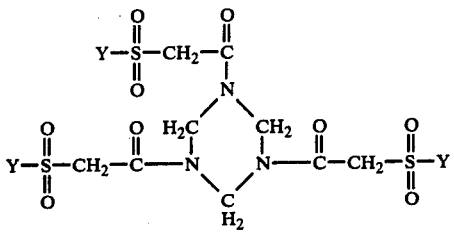 (II)
wherein Y represents a vinyl group; A represents a divalent group; R, which may be the same or different, each represents a hydrogen atom or a hydrocarbon group having 1 to 4 carbon atoms; and $n$ is 0 or 1.
* * * * *